United States Patent [19]

Doyle

[11] Patent Number: 5,051,551
[45] Date of Patent: Sep. 24, 1991

[54] IMMERSION PROBE FOR INFRARED INTERNAL REFLECTANCE SPECTROSCOPY

[75] Inventor: Walter M. Doyle, Laguna Beach, Calif.

[73] Assignee: Axiom Analytical, Inc., Laguna Beach, Calif.

[21] Appl. No.: 596,469

[22] Filed: Oct. 12, 1990

Related U.S. Application Data

[63] Continuation-in-part of Ser. No. 353,969, May 18, 1989, abandoned.

[51] Int. Cl.$^5$ .................... G01N 21/35; G01N 21/85
[52] U.S. Cl. .................................. 250/341; 250/343
[58] Field of Search .............. 356/244, 440, 300; 250/341, 343, 573, 574

[56] References Cited

U.S. PATENT DOCUMENTS

| | | | |
|---|---|---|---|
| 3,164,663 | 1/1965 | Gale | 250/574 X |
| 3,370,502 | 2/1968 | Wilks, Jr. | 356/133 |
| 3,751,672 | 8/1973 | Michel et al. | 250/574 X |
| 4,595,833 | 6/1986 | Sting | 250/353 |
| 4,826,313 | 5/1989 | Schär et al. | 356/51 |

OTHER PUBLICATIONS

The Infrared Handbook, Revised Edition, Environmental Research Institute of Michigan, 1985, pp. 9.12–9.13.

Primary Examiner—Constantine Hannaher
Assistant Examiner—Edward J. Glick
Attorney, Agent, or Firm—Thomas J. Plante

[57] ABSTRACT

A probe is disclosed for use in internal reflection spectroscopy at locations immersed in containers. Two parallel light pipes, located inside the probe, are used to carry radiation toward and away from an internal reflectance element (IRE) located at or near the bottom of the probe. The IRE, which is exposed to analyte in the container, has a radiation-entering surface and a radiation-exiting surface which permit collimated radiation to fill both light pipes. No beamsplitter is required to separate pre-sample and post-sample radiation. In one embodiment the IRE is a rod having concave conical entering and exiting surfaces, and a separate radiation-direction-reversing element is mounted on the tip of the probe. In another embodiment the IRE is itself a direction-reversing means mounted on the tip of the probe.

32 Claims, 7 Drawing Sheets 5,051,551

IMMERSION PROBE FOR INFRARED INTERNAL REFLECTANCE SPECTROSCOPY

This application is a continuation-in-part of application Ser. No. 353,969, filed May 18, 1989 now abandoned.

BACKGROUND OF THE INVENTION

This invention relates to internal reflection spectroscopy; and its primary purpose is to provide an apparatus which permits relatively deep immersion of an internal reflectance accessory into a container whose contents are to be analyzed. The analysis is accomplished by attenuated total reflectance (ATR), for which an internal reflectance element (IRE) is used. For the range of materials of primary interest, the desired analytical radiation is mid-infrared (MIR).

In an earlier application, U.S. Ser. No. 158,214, filed Feb. 19, 1988, now U.S. Pat. No. 4,835,389, the inventor in the present application disclosed several versions of such an apparatus. The present application has a different assignee from U.S. Pat. No. 4,835,389.

The apparatus of U.S. Pat. No. 4,835,389 has a tube, or light pipe, extending into a container; an internal reflectance element (IRE) at the bottom of the tube (supported by the tube); and a beamsplitter outside the tube which directs radiation from a source through the tube to the IRE, and directs radiation returning from the IRE to a detector.

As explained in U.S. Pat. No. 4,835,389, there are major benefits obtainable from deep immersion spectroscopy. One of the most important uses is in "batch process kettles", wherein liquid in a container is processed. Such processing usually involves chemical reactions, but it might also involve the non-reactive mixing of ingredients. In such processing kettles, the availability of in-situ, real-time spectroscopic analysis during the processing period can be of great practical value. It can provide information as to the progress of the processing, thereby permitting timely determination that the process has been completed. It can also provide valuable insights leading to possible improvements in future processing procedures.

Another major use of deep immersion spectroscopy relates to material in "storage drums". Because of the problem of material changes (deterioration) due to lengthy storage, it is desirable (and may be required by laws or regulations) to be able to promptly analyze the current condition of the material. Furthermore, in the case of hazardous or highly reactive materials, it is often desirable to positively identify a material (independent of its labeling) prior to using it in a process.

The apparatus of U.S. Pat. No. 4,835,389 may be referred to as a "colinear path" design, because a single ended IRE is used. Both the radiation entering the IRE and the radiation leaving the IRE pass through the upper end of the IRE; and both the entering and returning beams are in the same passage, or light pipe, between the beam splitter and the IRE.

An important objective of the present invention is to increase the signal transmission (radiation throughput) for a given path length and light pipe diameter.

The disclosure of the parent application Ser. No. 353,969 showed a dual light pipe structure, in which the entering and returning beams travel in separate, parallel light pipes. An IRE is located at the lower end of the structure. Its preferred location was stated to be in the lower end of one of the light pipes. And a separate retroreflector device was included to reverse the direction of the light. Certain claims were broad enough to cover an arrangement in which the IRE itself constitutes the direction-reversing means. However, such a structure was not illustrated.

Three prior art patents cited in the parent application disclose immersion structures in which a generally cone-shaped structure was mounted at the end of an analytical device intended to be immersed in a liquid sample. Michel et al U.S. Pat. No. 3,751,672 discloses an immersible refractometer, which includes parallel light pipes (105 and 106 in FIG. 10) and a "probe tip" 104 having internal reflecting surfaces whose angles of incidence are less than the critical angle. Such a device is not relevant to spectroscopic analysis, but rather is used to measure the index of refraction of the sample.

Two other prior art patents cited in the parent application - Schar et al U.S. Pat. No. 4,826,313 and McLachlan et al U.S. Pat. No. 4,829,186 - disclose immersible devices for use in ATR spectroscopy. Each of those patents has an ATR tip immersed in liquid ("conical sapphire 1" in Schar; and "trapezoidal prism 9" in McLachlan).

A fundamental difference between the analytical purposes of the present application and those of the Schar and McLachlan patents is the radiation wavelengths for which they are intended. Both Schar and McLachlan use optical fibers to conduct light toward and away from the ATR element. Although there is a substantial body of art relating to the use of fiber optic probes in spectroscopic systems, such art is not useful for the purpose of the present invention. Its inapplicability is due to the fact that fiber optic transmission characteristics are not adequate for use in analyzing mid-infrared (MIR) wavelengths. However, MIR is by far the most useful spectral region for studying the properties of the organic molecules fundamental to fields ranging from polymers to pharmaceuticals.

The inapplicability of optical fiber light guides to MIR wavelengths is acknowledged in this quotation from an article relating to fiber optics by Degrandpre and Burgess in Applied Spectroscopy (Vol. 44, No. 2, 1990, page 274):

"The mid-IR fibers suffer from high material absorption and scattering and poor mechanical and chemical stability. Therefore, they are not well suited for polymer-clad evanescent field sensors in their present stage of development."

For reasons which will be discussed in detail below, the objectives of the present invention require light pipes, not optical fibers, as the radiation transmitting (and guiding) structures. The term "light guide" is generic, including both "light pipes" and "optical fibers", but the two species are fundamentally different.

Optical fibers are solid materials having an index of refraction which is higher than the surrounding medium. The surrounding medium could be air, or it could be any material having a lower index of refraction than the optical fiber. There is an interface between a material of a higher index and a material of a lower index. The light propagates through the material of higher index, and is at a high enough incidence angle so that it is totally reflected at the interface. There is total internal reflection as the light channels down through the optical fiber.

In the case of a light pipe, the light pipe either is a metallic material, or a material that is internally coated with a metal that is a good reflector. The light travels through air, which is a medium having a low index of refraction, and is reflected off the metallic surfaces as it travels down through the light pipe.

The operation of a light pipe is essentially independent of radiation wave length, since the radiation is propagating through either air, dry nitrogen, vacuum, or the like, so the medium the light is propagating through is relatively transparent at all wavelengths. In contrast, an optical fiber light guide has its wavelength coverage limited by the transmission ability of the solid material that is used. The materials that are used for fiber optics have much better transmission in the visible and near-infrared than they do in the mid-infrared. Most of them become very highly absorbing in the mid-infrared.

SUMMARY OF THE INVENTION

The present invention uses a dual light pipe structure (not optical fiber light guides), in which the entering and returning beams are transmitted in separate, parallel light pipes. No beamsplitter is required; and, therefore, the dual light pipe structure generally has two or three times greater radiation throughput than the co-linear path structure.

There is a trade off, in that the parallel light pipe structure requires a greater lateral space (outer tube size) for a given light pipe diameter.

In the present invention, the IRE (or ATR element) is a double-ended, rather than a single-ended, element. In other words, the beam coming from the source enters at one end of the IRE, and exits through the other end of the IRE on its return path to the detector.

Preferably the IRE is cylindrical in cross-section, and has two polished conical ends. Conical reflectors may be used at each end of the IRE, the reflectors being so arranged that radiation rays enter and leave the conical ends of the IRE at essentially perpendicular incidence.

In one version of the invention the IRE is the remote end of the immersion structure, and serves the additional purpose of reversing the direction of the infrared radiation.

The present invention is well-suited to function in the mid infrared (MIR) wavelength range, which is of primary importance in many analytical measurements.

DETAILED DESCRIPTION OF THE PREFERRED EMBODIMENT

Figure 1:
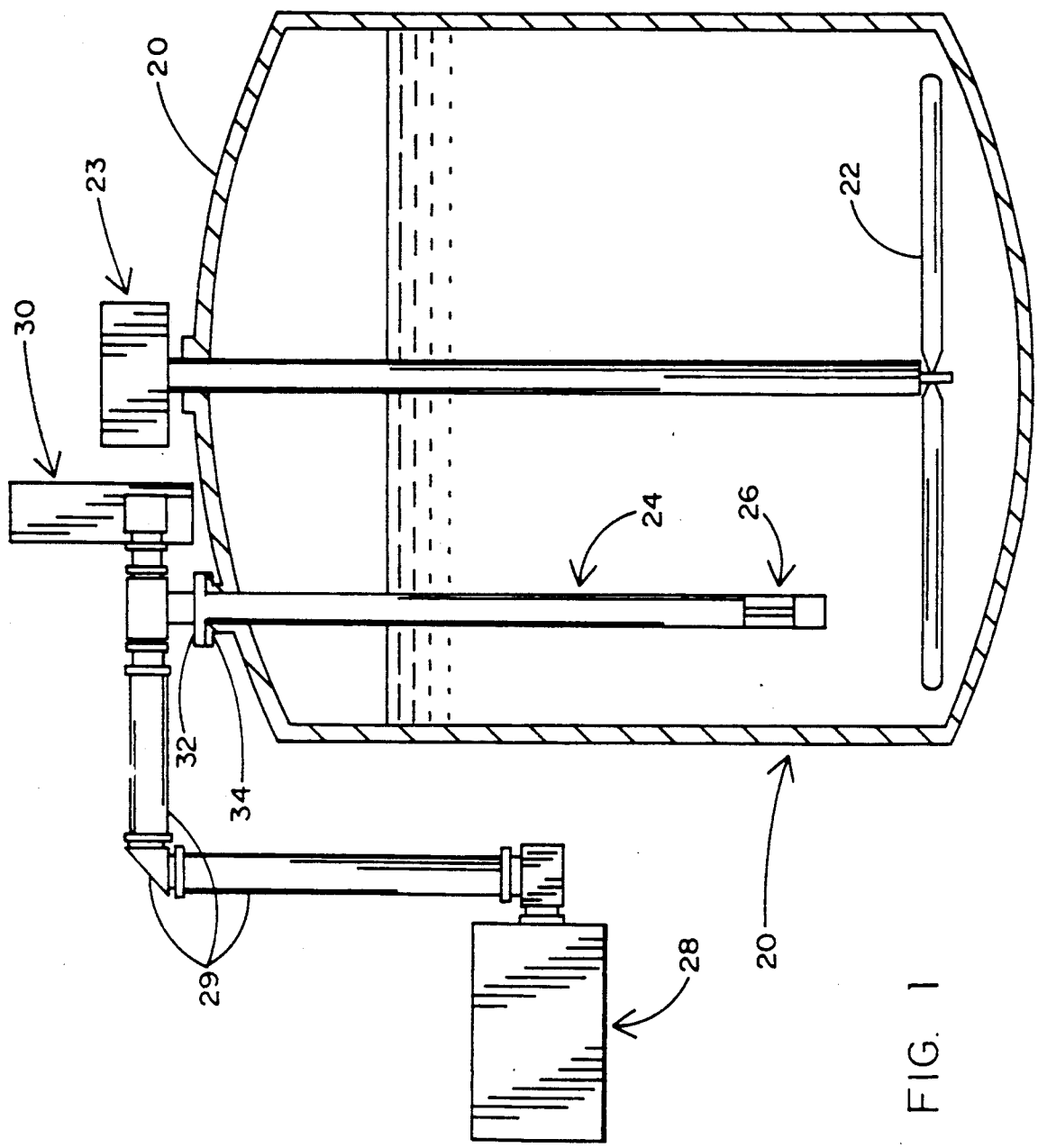
FIG. 1 shows the general arrangement of a reaction vessel having a deep immersion IRE probe.

FIG. 1, whose dimensions are not intended to represent the true relative sizes of the structural elements, supplies an understanding of one environment in which the present invention may be used. A large container 20 is shown, which is completely enclosed and sealed. An internal stirring paddle, or mixing blade, 22 is generally used, driven by an externally-located motor 23. The openings for supplying fluids to, and removing them from, the container are not shown in FIG. 1.

A spectrometer-associated probe for analysis of the material inside the container comprises a elongated tube 24 extending into the container, and an internal reflection element (IRE) 26 supported at the lower end of the tube. It is desirable to locate the IRE 26 as far down in the container 20 as possible, so that the analytical function can be performed even with a relatively small amount of material in the container.

Inside elongated tube 24, infrared radiation is directed downwardly and into IRE 26, and is returned upwardly to exit from the top of the tube, after it has been altered by its reflected contacts with the internal wall of IRE 26, where it is attenuated by partial absorption in the surrounding liquid sample. In FIG. 1, an FTIR spectrometer is shown at 28, external transfer optics at 29, and a detector at 30.

The tube 24 is supported by an integral annular flange 32, which rests on, and is secured to, a flange 34 provided on the top of container 20.

Figure 2:
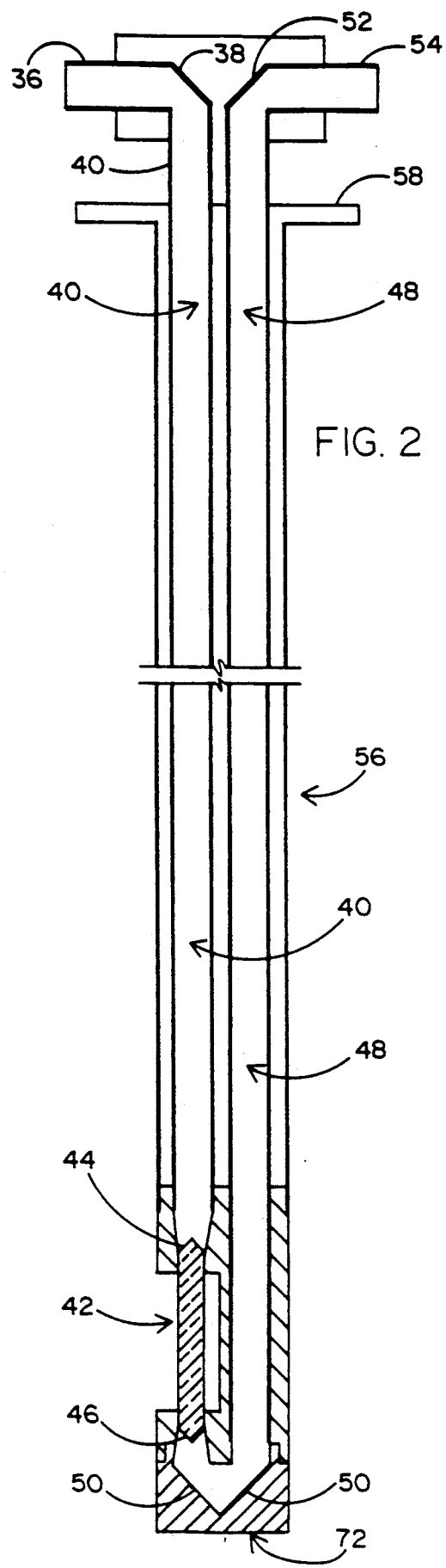
FIG. 2 shows in cross-section a deep immersion probe having parallel light pipes for conveying radiation to and from a double-ended IRE carried at the lower end of the tube.

FIG. 2 illustrates the dual (parallel) light pipe structure of the present invention. An entering collimated beam, from the FTIR spectrometer 28, passes through a horizontal tube 36, is reflected by a flat 45° mirror 38, and continues as a collimated beam down an elongated light pipe 40.

Mounted near the lower end of the light pipe 40 is an IRE (ATR crystal, or rod) 42. IRE 42 is a double ended element, i.e., radiation from the source enters the upper surface 44 of IRE 42, and sample modulated radiation directed to the detector exits through the lower surface 46 of IRE 42. Both the upper and lower ends of IRE 42 are polished conical surfaces, each of which is associated with a conical reflector, as discussed more fully below. The outer surface of IRE 42 is in contact with the sample material in container 20.

Modulated radiation leaving the lower end of IRE 42 is caused to return upwardly as collimated radiation through a light pipe 48 parallel to light pipe 40. The radiation leaving IRE 42 may be reflected by a concave conical retroreflector surface 50, which acts as a radiation direction reversing means. When the upwardly traveling collimated radiation reaches the top of light pipe 48, it is reflected by a flat 45 mirror 52 as a collimated beam through a horizontal tube 54 toward the detector 30. Other usable types of radiation direction reversing means are non-conical retroreflectors (e.g., cube corner reflectors), and inverted roof-top reflectors.

Because of the parallel paths of the entering and returning radiation, no beamsplitter is needed. The result is a major increase in radiation throughput over prior immersion structures. Because two light pipes are used, the overall diameter of the immersion structure is essentially doubled.

The use of a radiation direction reversing means, such as the conical retroreflector 50, causes the upwardly-traveling radiation to return accurately on a path parallel to the downwardly-traveling radiation. The 90° retroreflector cone is particularly effective for rays parallel or nearly parallel to the axis of the cone; but there is some loss in optical quality for rays traveling at an angle to the cone axis.

If desired, IRE 42 may be mounted at the lower end of the light pipe 48, instead of light pipe 40. In other words, the IRE could receive radiation which is starting on its upward path, after reflection by retroreflector cone 50. In that case, collimated radiation would travel downwardly through light pipe 40 the full length of the probe, and enter the IRE only after reflection by cone 50.

The parallel light pipes 40 and 48 are surrounded by an outer tube (probe) 56, which may be either circular or rectangular in cross-section. Generally, a circular shape is preferred. The space inside the outer tube is used to contain a purged atmosphere, e.g., nitrogen, in order to obtain data which has not been influenced by variable ambient conditions. The outer tube 56 has an integral annular flange 58 at its upper end, which is supported by the top of the container (as in FIG. 1), and in turn provides support for the tubular structure which extends downwardly into the container. Flange 58 has two round openings through which the light tubes 40 and 48 extend.

Figure 3:
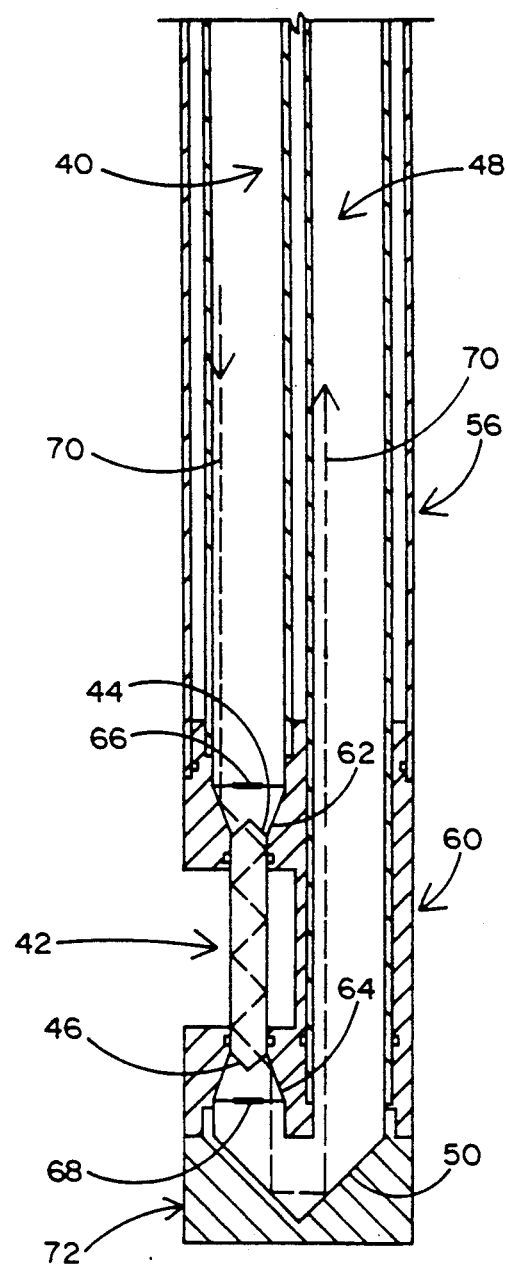
FIG. 3 is an enlarged and detailed cross-section of the preferred structure at the lower end the tube of FIG. 2.

FIG. 3 is an enlarged cross-section of the lower end of the deep immersion probe. A metal support 60 is provided at the lower end of tube 56 to support the IRE 42 (which is commonly referred to as the ATR crystal, or rod). The entire tubular structure may be held together longitudinally by a single long screw (not shown), e.g., four feet long, extending from the metal mounting structure 60 to the flanged cover 58 at the upper end.

The preferred structure of the IRE and its associated reflecting cones is that disclosed in common inventor, common assignee U.S. patent application Ser. No. 312,130, filed Feb. 17, 1989. The beams entering and exiting the IRE are preferably collimated, although nominally focusing beams may be used.

The IRE 42 has a circular cross-section. Its entering end 44 and its exiting end 46 have convex conical polished surfaces. A concave conical reflector surface 62 is positioned at the IRE entering end 44; and a concave conical reflector surface 64 is positioned at the IRE exiting end 46.

In order to maximize IRE performance, it is necessary to limit the transmitted rays to those which: (a) strike the adjacent conical reflector once; and (b) enter and exit the IRE on paths substantially perpendicular to the conical end surfaces of the IRE.

As explained in U.S. Ser. No. 312,130, these results can be accomplished by combining two concepts: (a) limiting the large end diameter of each of the conical reflectors 62 and 64; and (b) using a centered optical stop, or radiation blocking element, at the large diameter end of each conical reflector. In FIG. 3, the optical stop for conical reflector 62 is shown at 66; and the optical stop for conical reflector 64 is shown at 68. The centered optical stops 66 and 68 may be supported by suitable spider arms. The limitation of the large end diameter of each conical reflector essentially cuts off rays which would be reflected twice by the conical reflector. And the central radiation blocking element essentially cuts off rays which would not be reflected by the conical reflector.

The disclosure of U.S. Ser. No. 312,130 is included herein by reference, in order to provide a more detailed explanation of the principles just discussed.

The present invention, which uses radiation direction reversing means and two light pipes, could, however, be applied to an IRE having a different structure from that disclosed in U.S. Ser. No. 312,130.

The radiation which travels down light pipe 40 is reflected by conical reflector 62 into the upper conical end 44 of IRE 42. After several reflections from the inner wall of the IRE, the radiation exits from the lower conical end 46 of the IRE, and is reflected by conical reflector 64. Both the entering and exiting radiation at the conical reflectors is essentially collimated, and it fills both light tubes.

Radiation leaving conical reflector 64 is reflected by the concave conical retroreflector surface (retroreflector cone) 50. The retroreflector directs the radiation upwardly along a parallel path in light pipe 48. A dashed line 70 having directional arrows illustrates the path of a single ray traveling downwardly in light pipe 40, passing through the IRE, and traveling upwardly in light pipe 48. As stated above, the direction of the ray represented by dashed line 70 could be reversed, if the source and detector connections were reversed.

The retroreflector cone 50 may be formed as a surface in a metal end cap 72, which is secured (e.g., by a threaded connection) to the lower end of metal support 60. The retroreflector cone is preferably coated with a highly reflective material which does not tarnish, such as gold. The interior walls of light pipes 40 and 48 also are coated or polished to minimize radiation absorption.

All of the exterior surfaces of the tubular probe which are exposed to the materials in container 20 should be formed of corrosion-resistant material, e.g., stainless steel. This includes tube 56, metal support 60, and end cap 72. The IRE 42 is formed of a suitable crystalline material, such as zinc selenide. The interior of the tubular probe is sealed from the liquids in container 20 by O-ring seals located near each end of IRE 42 and in sealing engagement with the exterior of the IRE.

Figure 4:
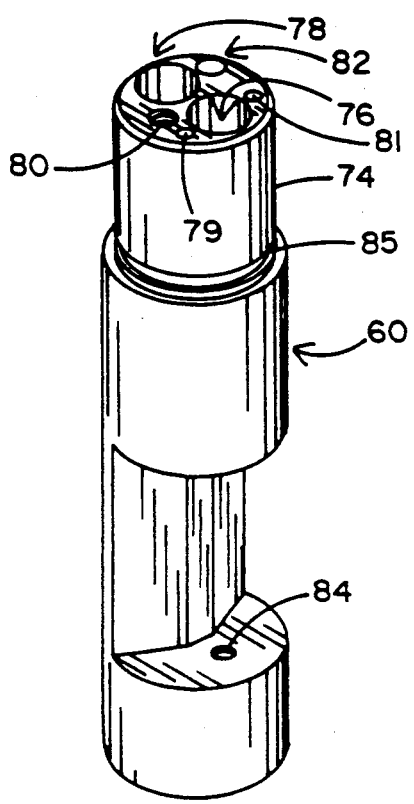
FIG. 4 is an isometric drawing which shows a mechanical element used to retain the IRE and associated parts.

FIG. 4 is an isometric view of the metal support 60, which illustrates the relative positions of the light pipes and other elements inside the outer cylindrical surface of the probe. At its upper end, metal support 60 has vertical openings which are provided to serve various functions. Openings 76 and 78 receive, respectively, light tubes 40 and 48. Opening 80, which is internally threaded, has the lower end of the long connecting screw in threaded engagement with it. Opening 82 is a passage for purging gas. Near the lower end of FIG. 4, an opening 84 is shown, into which the lower end of the IRE extends. A groove 85 in the periphery of support 60 is provided to receive an O-ring seal, which also engages the outer tube 56. Two additional small openings 79 and 81 are provided. They are threaded openings which receive screws used to retain a thin plate (not shown) against the upper surface of metal support member 60. The plate has holes corresponding to those in member 60. The reason for using a separate flat plate at the top of member 60 will be explained in conjunction with the following description of FIG. 7.

Figure 7:
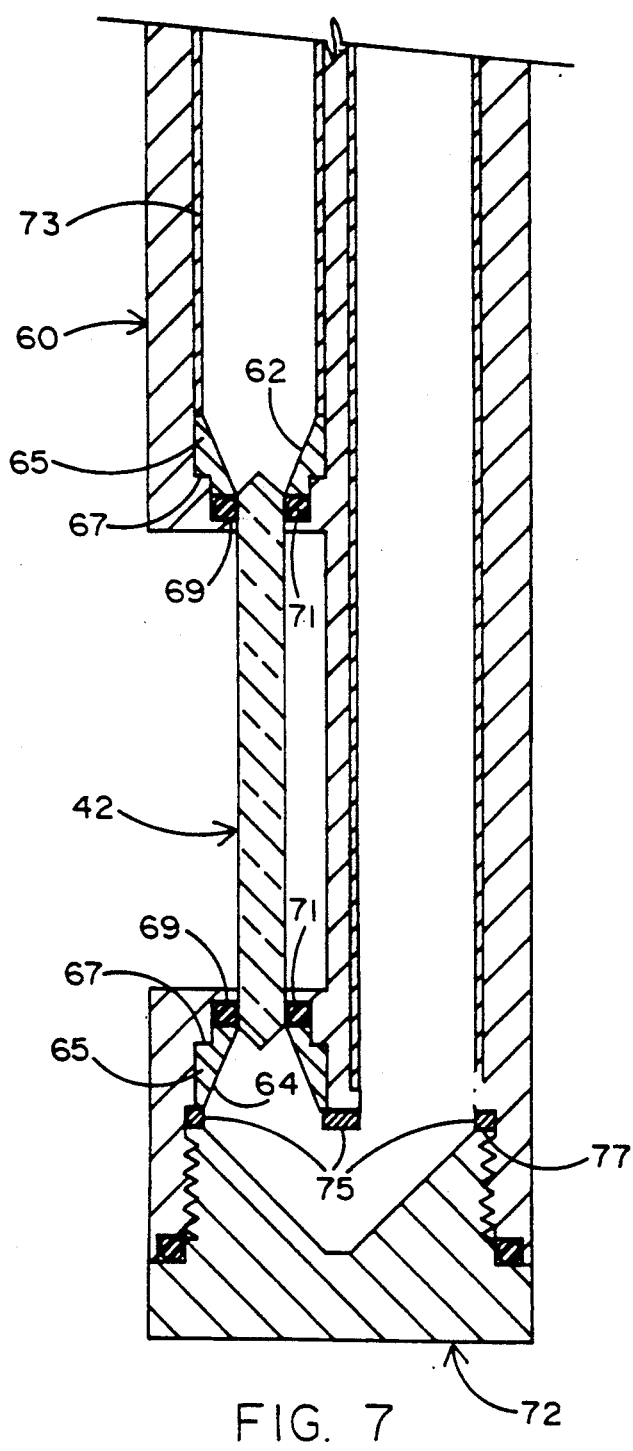
FIG. 7 is a close-up of the mechanical elements in the sensing head which contains the IRE and adjacent reflecting surfaces.

FIG. 3 does not show the mechanical details of the parts which provide conical reflectors 62 and 64; nor does it show how those parts are retained in position. FIG. 7 is provided to clarify those details. As seen in FIG. 7, each conical reflector surface 62 and 64 is formed inside a machined element 65. The outer cylindrical surface of each element 65 has a stepped, or notched, portion which is adapted to engage a shoulder 67 formed in member 60. Member 60 also has an annular recess 69 formed near each end of IRE 42. Located in each recess 69 is an O-ring 71, which is used to seal and also retain in position one end of the IRE.

Each of the elements 65 is urged into engagement with shoulder 67, in which position it compresses the respective O-ring 71, causing the latter to grip tightly the periphery of the IRE. The upper element 65 is engaged and held in place by a section 73 of light pipe, which terminates at the top of member 60 (FIG. 4) and is retained in position by the flat plate referred to above. A separate section of light pipe is located between that flat plate and the top of the probe.

The lower element 65 is engaged and held in place by another flat plate 75, which is engaged by the upper end 77 of the threaded end cap 72.

The details just described are intended to ensure proper relative positioning of the IRE and the conical reflecting surfaces 62 and 64. The radiation blocking elements 66 and 68 have been omitted from FIG. 7. They are provided as very thin elements which are separate from elements 65, and which have spider arms peripherally retained between the large diameter ends of elements 65 and the adjacent surfaces.

Figure 6:
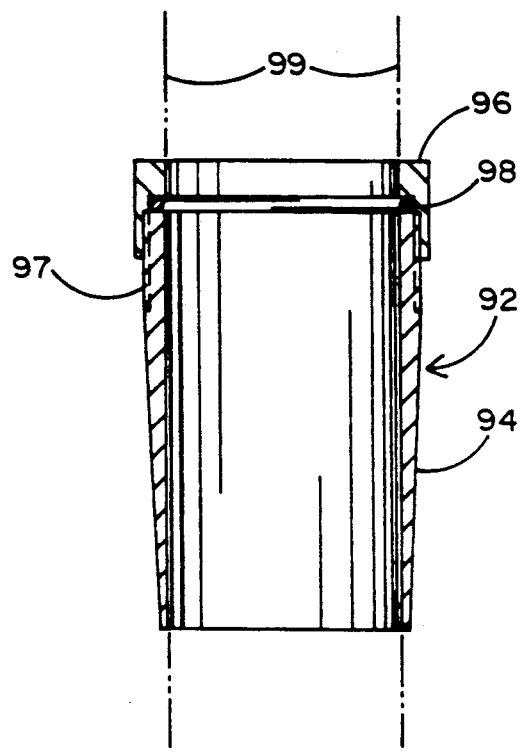
FIG. 6 is a close-up view of a portion of FIG. 5.
Figure 5:
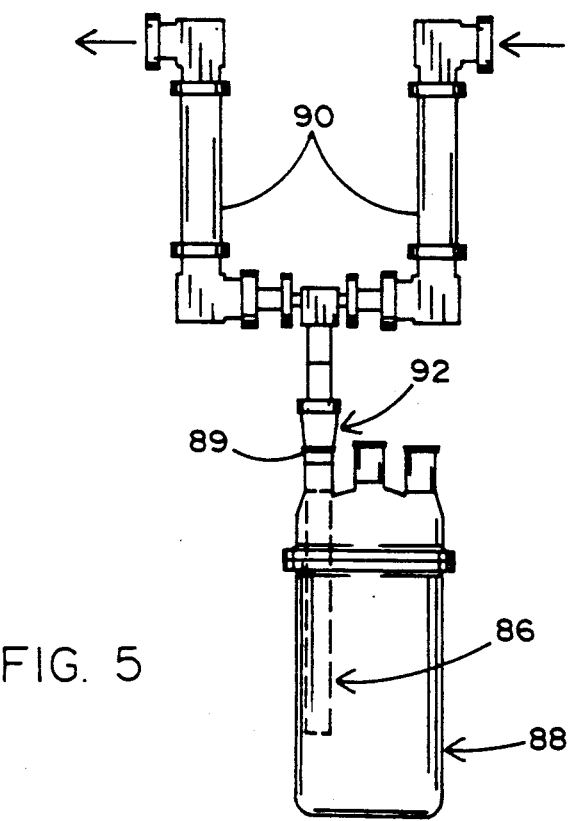
FIG. 5 shows another embodiment of the invention, which is designed for use in smaller containers.

FIGS. 5 and 6 relate to a relatively small immersion probe, which may be used in a laboratory reaction vessel. The large scale probe of FIGS. 1-4 may, for example, be 2 inches or 4 inches in diameter, and up to 8 feet long. The small probe of FIGS. 5-6 may, for example, be 1 inch in diameter, and 16 inches long.

The probe in FIG. 5 has the same functional characteristics as the larger probes. A probe 86 extends into a relatively small reaction vessel 88, through an opening 89. External transfer optics are shown at 90. A tapered joint 92, through which the upper end of probe 86 extends, provides a sealing fit with a tapered access opening 89 in the reaction vessel 88.

The depth to which probe 86 extends in vessel 88 is adjustable by moving the probe vertically with respect to joint 92 (see FIG. 6). After the desired position of the probe has been established, it will be held in place by turning an annular nut 96, which has threaded engagement with an upper non-tapered portion 97 of joint 92. As nut 96 moves downwardly with respect to portion 97 of joint 92, an O-ring 98 is pressed between the top of joint 92 and the bottom of nut 96. This causes the O-ring to spread horizontally into tight engagement between the outer surface of probe 86 (shown by vertical broken lines 99) and the inner wall of nut 96, thus holding the probe in the selected position. Turning nut 96 to move it upwardly releases the grip of the O-ring, permitting relocation of the probe.

Figure 8:
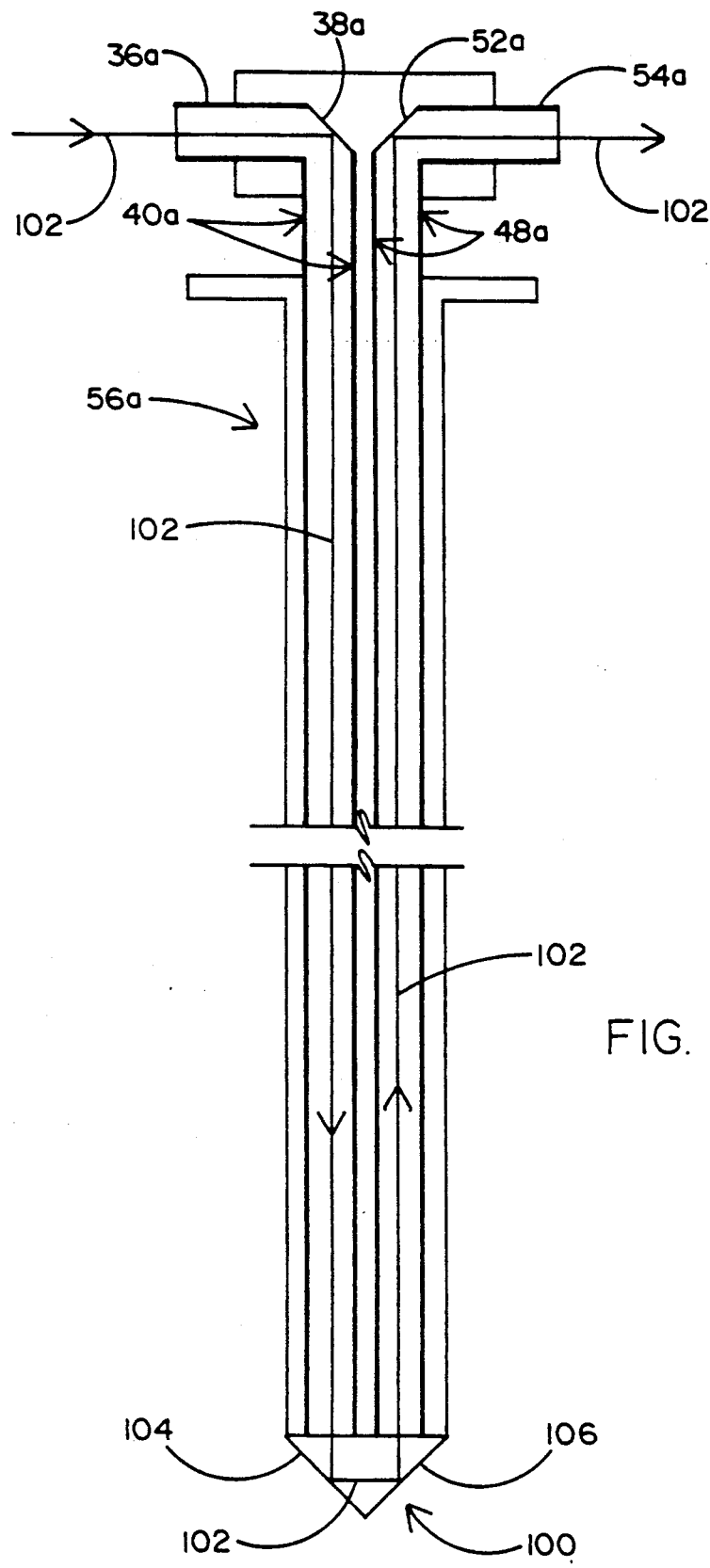
FIG. 8 shows a different embodiment of the invention, in which the IRE also functions as the means for reversing the direction of the radiation.
Figure 9:
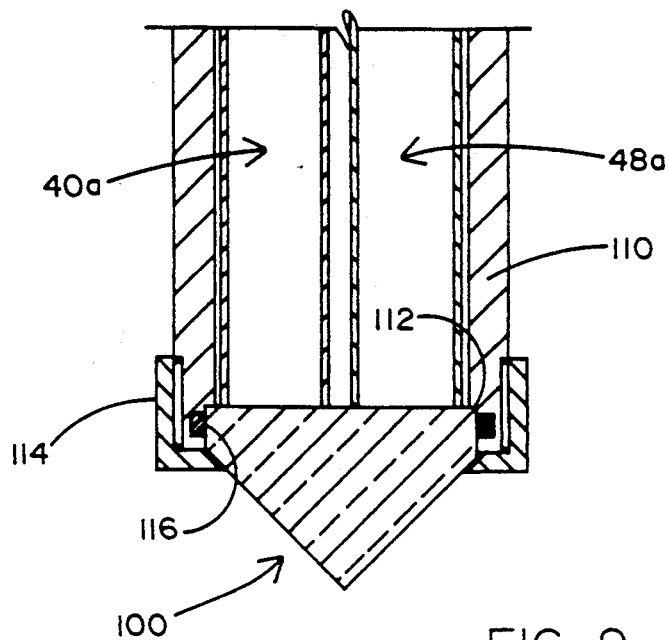
FIG. 9 is a detailed showing of the lower end of the probe of FIG. 8.

FIGS. 8 and 9 disclose another embodiment of the invention, in which the IRE serves the dual purposes of (a) providing ATR information and (b) reversing the direction of the infrared radiation between the two light pipes.

FIG. 8 is similar to FIG. 2, except that the IRE in FIG. 8 is an element 100 so shaped that it constitutes the remote (usually bottom) end of the immersible structure (probe). In FIG. 8, element 100 is a two-reflection ATR element, the outer surface of which is in contact with the sample material. Each reflection inside ATR element 100 is at an angle of incidence above the critical angle. As shown, the two ATR reflections are at the desirable angle of 45°. In FIG. 8, as in FIG. 2, an entering collimated beam (represented by axial ray 102), from the FTIR spectrometer, passes through a horizontal tube 36a, is reflected by a flat 45° mirror 38a, and continues as a collimated beam down an elongated light pipe 40a. Light pipe 40a is supported in a tube-like probe 56a extending into a container.

Mounted on the lower end of the probe 56a is the IRE (ATR crystal) 100. IRE 100 may be either a retro-reflector or an inverted roof-top. The conical shape is considered preferable. As shown by ray 102, the downwardly traveling IR radiation impinges on one side of IRE 100 at 104, travels horizontally to impinge on the opposite side of IRE 100 at 106, and then is reflected upwardly inside a light pipe 48a, which is parallel to light pipe 40a.

The modulated radiation leaving the IRE 100 returns upwardly as collimated radiation through light pipe 48a. When the upwardly traveling collimated radiation reaches the top of light pipe 48a, it is reflected by a flat 45° mirror 52a as collimated beam 102 through a horizontal tube 54a toward the detector.

FIG. 9 shows the primary elements at the lower end of the probe in FIG. 8. A metal supporting structure 110, similar to structure 60 in FIG. 4, may be used to enclose light pipes 40a and 48a. At the lower end of support 110, the IRE 100 has its upper surface clamped against a shoulder 112 formed in support 110. An internally threaded cap 114 holds IRE 100 against shoulder 112. An O-ring 116 provides a seal between IRE 100 and support 110.

The versatility of the immersion probes described in this application is indicated by their availability with dimensions ranging from 1 inch in diameter and 16 inches in length to 4 inches in diameter and 8 feet in length, with the larger probes intended for use in large scale reactors. The smaller probes are compatible with a variety of tasks, ranging from monitoring laboratory and pilot scale reactions to the identification of hazardous waste and other stored chemicals.

The following are general criteria followed in providing the herein described deep immersion probes:

1. The probe and optical transfer system should have as high a radiation transmission as possible and should not require optical alignment.

2. The IRE sampling device should provide highly repeatable data with a linear dependence of absorbance on analyte concentration.

3. All elements of the probe should function properly under the thermal, mechanical, and chemical conditions encountered in a typical batch reactor.

In general, the probe will be expected to operate deeply immersed in a reaction vessel, and in many cases will be subjected to varying bending torques, vibration, and changes in temperature.

Because of the citation of optical fiber light guides against the parent application, it apparently is desirable to describe the fundamental differences of light pipe systems of the type disclosed in this application.

There are two fundamental obstacles to the use of fiber optics in the mid-IR wavelength range: (1) basic material properties, and (2) the need for very high geometric throughput (TP) in this spectral region.

(1) The fundamental vibration modes of most molecules fall in the MIR. This is the reason that MIR is by far the most useful spectral region for studying the properties of the organic molecules fundamental to fields ranging from polymers to pharmaceuticals. But this very factor, which makes MIR so attractive for spectroscopy, works counter to the use of fiber optics in this region. The fact is that virtually all of the materials that would be attractive for use as optical fibers have fundamental lattice vibrations which absorb in the MIR. As a result, practical MIR fibers have not been developed.

(2) MIR radiation sources are generally quite weak compared to sources available in other regions of the spectrum. At the same time MIR detectors are relatively insensitive. These two factors together place a very high premium on achieving a very high geometrical throughput in any optical system designed for use in the MIR. Throughput is defined as the product of the area of an aperture and the solid angle distribution of the radiation passing through that aperture. The range of angles that an optical system will transmit is usually specified by a quantity called its numerical aperture (NA). The limiting throughput of a fiber optic system will thus be proportional to the area of the fiber times the square of its NA.

With visible and near infrared (NIR) systems, the sources are so powerful and the detectors are so sensitive that fiber TP is usually not a significant factor. In the MIR, however, TP must be maximized. In a non-fiber system, the limiting TP will often be determined by practical detector sizes. For example, a system using a broadband room temperature pyroelectric detector will typically have a detector diameter of 1 mm and detector collecting optics with a numerical aperture of 0.5 or slightly higher (i.e., 60° field-of-view). To make full use of the TP of the detector sub-system, a fiber optic system should have an equal or greater TP. Since a NA of roughly 0.5 is also a maximum practical value for coupling radiation into a fiber, this would require a fiber core diameter of at least 1 mm. Fibers with this great a diameter would probably be too stiff and hence fragile to be practical. The use of a fiber bundle would not be a good solution to this problem because the necessary cladding and gaps between the fibers would occupy a significant proportion of the collecting area.

The present invention solves the problem of communicating with a sensing element immersed in a chemical medium by using metallic-coated light pipes having dimensions which are large compared to the dimensions of practical optical fibers. The use of light pipes eliminates the first problem (item 1), above, since the metal coatings used do not have strong absorptions in the mid-IR. This is in part due to the electrical conductivity of the metals which gives rise to high IR reflectance.

The relatively large size of the light pipes eliminates the throughput limitation (item 2). Moreover, there is an additional benefit of using relatively large dimension light pipes with the conical IRE of FIG. 9, which benefit is related to the practical design considerations involved in interfacing the light guide with the sensing element.

Figure 10:
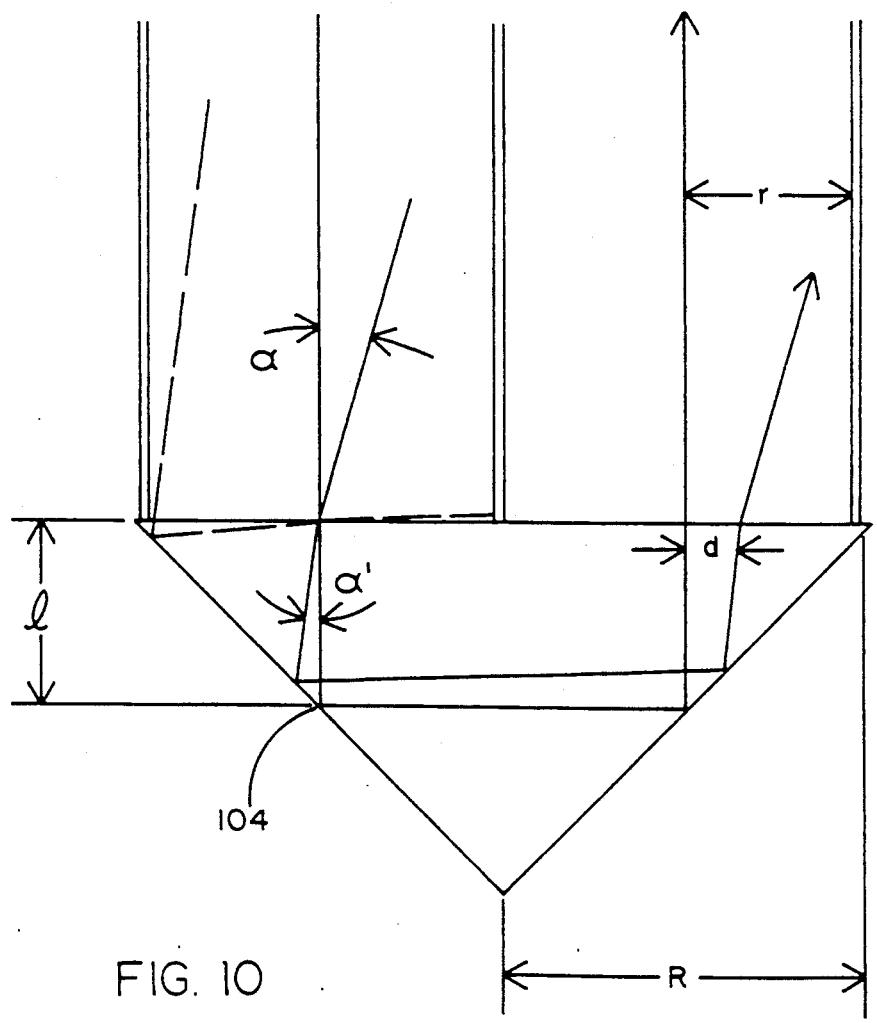
FIG. 10 shows schematically the effect of light guide dimensions on the amount of radiation lost due to the divergence angle.

FIG. 10 illustrates the paths followed by selected rays in the IRE. The desirable incidence angle of 45° shown in these illustrations can be achieved with an IRE which is in the form of either a two faceted "roof top" or a circular cone. FIG. 10 is an idealized case, in which the light pipes have negligible wall thickness, and the total path length in the IRE is minimized. The following analysis concerns the amount of beam spread that occurs between the output of the first light pipe and the input to the second. This will be an indication of the amount of light that is lost. If a light pipe radius of "r" is assumed, it can be seen from FIG. 10 that the minimum radius (R) of the IRE is $R=2r$. By inspection it appears that, for an axial ray, the minimum path length (L) in the IRE will be $L=4l=2R=4r$, where "l" is the distance between the IRE entering point and the first reflection at 104. Considering a ray traveling through the light pipe at an angle of $a$ relative to the axis, on entering the IRE the divergence angle will reduced to $a'$, where $\sin a' = (1/n) \sin a$, assuming "n" is the index of refraction of the IRE. The lateral displacement (d) of this ray on traversing the IRE will be at least equal to $d = L \tan a' \geq L \sin a'$.

The foregoing information can be used to compare the performance of systems having the same light guide throughput but different diameters. In order to maintain throughput in an optical system using non-coherent light, the divergence angle will have to be scaled inversely proportional to the light guide diameter For example, consider a 10 mm light guide conducting radiation with a maximum divergence angle of 3° ($\sin 3° = 0.052$). To conduct this same optical power through a 1 mm diameter light guide would require a maximum divergence angle of 32° ($\sin 32° = 0.52$).

Using a 10 mm light guide and a 3° beam divergence with the idealized conditions of FIG. 10 would result in a total displacement of 1 mm on traversing the conical IRE. This is acceptable when the receiving light guide has a diameter of 10 mm, as in the case of metallic light pipes. However, if we reduce the diameter of the light guide to 1 mm (which is still large compared to practical fibers), and use a 32° divergence angle, the total displacement will be 1.25 mm. This will result in a very substantial loss with the 1 mm diameter fiber assumed.

The limiting case just discussed was the extreme one in which the light guide wall thickness was negligible. In reality, optical fibers normally have a cladding which is comparable in thickness to the radius of the light transmitting core. In addition, the IRE needs to have extra material for mounting surfaces. Both of these factors would serve to further reduce the optical transmission to be achieved with a fiber optic system.

Figure 11:
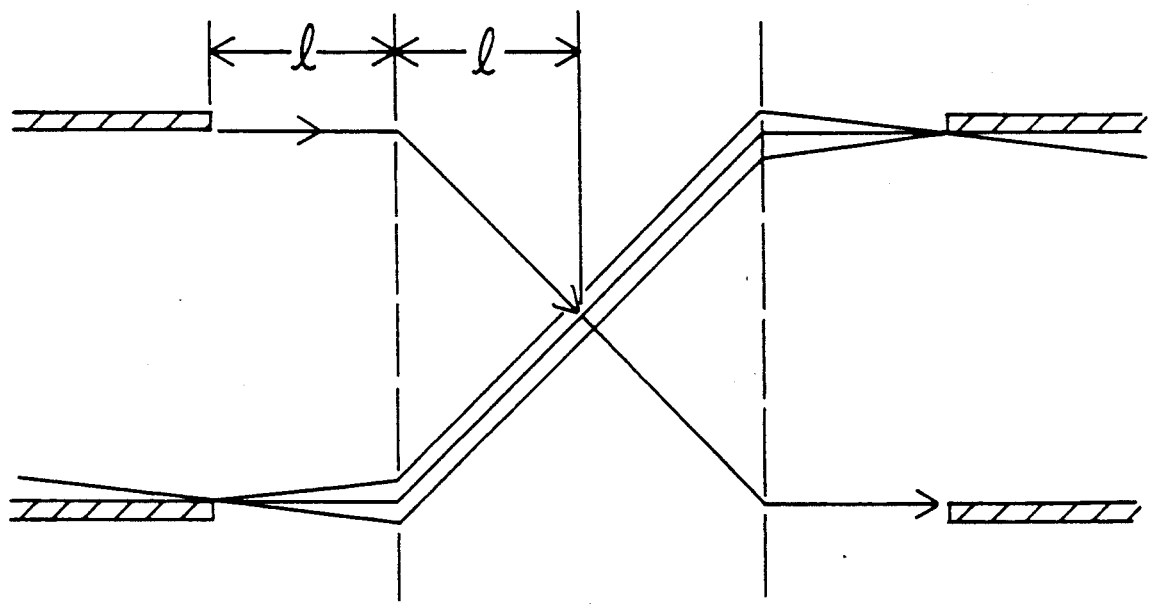
FIG. 11 illustrates the ray distribution and reduced vignetting obtainable with a cone-shaped radiation direction reversing means.

FIG. 11 illustrates the throughput benefits of using a cone-shaped reflecting element at the tip of the probe. Taking a cross-section perpendicular to the axis of the reflector, the properties of the roof-top and the cone will differ. In the case of the roof top, an angled ray such as the one illustrated in FIG. 10 will diverge continuously, just as it does in an axial plane. However, this is not the case with the cone.

One property of a retroreflecting cone is that every ray which initially propagates parallel to the axis will pass through the axis after reflection. Thus, in a given perpendicular plane, the cone acts much like a spherical lens having a focal length equal to the distance from its surface to the axis. This situation is illustrated schematically in FIG. 11. Here the paths of three rays diverge in such a way that they strike the cone along a line of intersection in a plane perpendicular to the system axis. For the sake of illustration, the path has been folded into a flat plane, with the two light pipes shown as if they were in this plane. The system is analogous to one in which the opposing conical surfaces are replaced by two lenses with focal length 1. For the idealized conditions of FIG. 11, the distance from the end of the light pipe to the equivalent lens position is also 1. It can be shown that under these conditions, a point at the output of the transmitting light pipe will be imaged at a corresponding point on the input of the receiving light pipe. Thus, under these ideal conditions, there will be no vignetting in this plane. As a result, the losses due to beam spread will be less in the case of a cone than in the case of a roof top.

From the foregoing description, it will be apparent that the structures disclosed in this application will provide the significant functional benefits summarized in the introductory portion of the specification.

The following claims are intended not only to cover the specific embodiments and methods disclosed, but also to cover the inventive concepts explained herein with the maximum breadth and comprehensiveness permitted by the prior art.

What is claimed is:

1. An internal reflection spectroscopy system for in-situ mid-infrared spectral analysis of sample material confined in a container, comprising:
   a source of mid-infrared analytical radiation which is directed toward the sample;
   a detector which receives sample-altered mid-infrared radiation from the sample;
   an elongated probe extending from the top of the container a substantial distance toward the bottom of the container, and into the sample material;
   a first hollow internally reflecting light pipe located inside the probe and extending substantially the full length of the probe, said first light pipe receiving radiation from the source;
   a second hollow internally reflecting light pipe located inside the probe and extending substantially the full length of the probe, said second light pipe transmitting radiation to the detector;
   an ATR internal reflectance element located near the lower end of the tube and exposed to the sample material;
   radiation from the source entering the internal reflectance element after traveling in one direction in the first light pipe;
   radiation to the detector exiting the internal reflectance element in order to travel in the opposite direction in the second light pipe; and
   radiation direction reversing means at the lower end of the probe for reversing the direction of the radiation, so that it travels along substantially parallel paths in the respective light pipes, causing source-supplied, sample-attenuated radiation to reach the detector.

2. The spectroscopy system of claim 1 in which:
   the radiation direction reversing means is a concave conical retroreflector.

3. The spectroscopy system of claim 2 in which:
   the internal reflectance element is located between the lower end of the first light pipe and the retroreflector.

4. The spectroscopy system of claim 2 in which:
   the internal reflectance element is located between the lower end of the second light pipe and the retroreflector.

5. The spectroscopy system of claim 1 in which:
   the internal reflectance element is located between the lower end of the first light pipe and the radiation direction reversing means.

6. The spectroscopy system of claim 1 in which:
   the internal reflectance element is located between the lower end of the second light pipe and the radiation direction reversing means.

7. The spectroscopy system of claim 1 in which:
   the internal reflectance element functions as the radiation direction reversing means.

8. The spectroscopy system of claim 7 in which:
   the internal reflectance element is a concave reflecting element mounted on the end of the probe which extends into the sample material.

9. The spectroscopy system of claim 7 in which:
   the infrared radiation entering the internal reflectance element from one direction is reflected by one side of the element to the other side of the element, and is then reflected by the element in the reverse direction.

10. The spectroscopy system of claim 7 in which:
    the radiation in both the first and second light pipes is essentially collimated and fills both light pipes.

11. The spectroscopy system of claim 1 in which:
    the infrared radiation enters the internal reflectance element at one end of the element and exits at the other end of the element.

12. The spectroscopy system of claim 1 in which:
    the internal reflectance element is a cylindrical rod having a convex conical radiation-transmitting surface at each end.

13. The spectroscopy system of claim 12 which also comprises:
    a concave conical reflector which reflects entering radiation into one end of the internal reflectance element.

14. The spectroscopy system of claim 13 which also comprises:
    a concave conical reflector which reflects radiation exiting from one end of the internal reflectance element.

15. The spectroscopy system of claim 12 in which:
    the radiation in both the first and second light pipes is essentially collimated and fills both light pipes.

16. The spectroscopy system of claim 1 in which:
    the radiation in both the first and second light pipes is essentially collimated and fills both light pipes.

17. The spectroscopy system of claim 1 which also comprises:
    a first flat mirror which reflects and redirects radiation from the source into the first light pipe; and
    a second flat mirror which reflects and redirects radiation from the second light pipe toward the detector.

18. The internal reflection spectroscopy system of claim 17 in which:
    the radiation reflected by both the first and second flat mirrors is essentially collimated.

19. For use in a spectral analysis system having a mid-infrared radiation source, an interferometer which receives such radiation from the source, a container having a liquid sample, and a detector which receives sample-modulated mid-infrared radiation, an immersion probe comprising:
    an elongated probe extending from the top of the container a substantial distance toward the bottom of the container, and into the sample material;

a first hollow internally reflecting light pipe located inside the probe and extending substantially the full length of the probe, said first light pipe receiving radiation from the source;

a second hollow internally reflecting light pipe located inside the probe and extending substantially the full length of the probe, said second light pipe transmitting radiation to the detector;

an ATR internal reflectance element (IRE) located near the lower end of the probe and exposed to the sample material;

radiation from the interferometer entering the IRE after traveling through the first light pipe;

radiation to the detector exiting the IRE in order to travel through the second light pipe; and radiation direction reversing means at the lower end of the probe for reversing the direction of travel of the radiation, so that it travels along substantially parallel paths in the respective light pipes, causing source-supplied, sample-attenuated radiation to reach the detector.

20. The immersion probe of claim 19 in which:
the radiation direction reversing means is a retroreflector 21. The immersion probe of claim 20 in which:
the radiation direction reversing means is a concave conical retroreflector.

22. The immersion probe of claim 19 in which:
the radiation direction reversing means is an inverted roof-top reflector.

23. The immersion probe of claim 19 in which:
the IRE is located between the lower end of the first light pipe and the radiation direction reversing means.

24. The immersion probe of claim 19 in which:
the IRE is located between the lower end of the second light pipe and the radiation direction reversing means.

25. The immersion probe of claim 19 in which:
the IRE functions as the means for reversing the direction of travel of the radiation.

26. The immersion probe of claim 19 in which:
the IRE is a cylindrical rod having a convex conical radiation-transmitting surface at each end.

27. The immersion probe of claim 26 which also comprises:
a concave conical reflector which reflects entering radiation into one end of the IRE.

28. The immersion probe of claim 27 which also comprises:
a concave conical reflector which reflects radiation exiting from one end of the IRE.

29. The immersion probe of claim 26 in which:
the radiation in both the first and second light pipes is essentially collimated and fills both light pipes.

30. The immersion probe of claim 29 in which:
the radiation reflected by both the first and second flat mirrors is essentially collimated.

31. The immersion probe of claim 19 in which:
the radiation in both the first and second light pipes is essentially collimated and fills both light pipes.

32. The immersion probe of claim 19 which also comprises:
a first flat mirror which reflects and redirects radiation from the source into the first light pipe; and
a second flat mirror which reflects and redirects radiation from the second light pipe toward the detector.

* * * * *